(12) United States Patent
Eggers et al.

(10) Patent No.: US 6,179,824 B1
(45) Date of Patent: *Jan. 30, 2001

(54) SYSTEM AND METHODS FOR ELECTROSURGICAL RESTENOSIS OF BODY LUMENS

(75) Inventors: Philip E. Eggers, Dublin, OH (US); Hira V. Thapliyal, Los Altos, CA (US)

(73) Assignee: ArthroCare Corporation, Sunnyvale, CA (US)

(*) Notice: Under 35 U.S.C. 154(b), the term of this patent shall be extended for 0 days.

This patent is subject to a terminal disclaimer.

(21) Appl. No.: 08/874,173

(22) Filed: Jun. 13, 1997

Related U.S. Application Data

(62) Continuation-in-part of application No. 08/561,958, filed on Nov. 22, 1995, now Pat. No. 5,697,882, which is a continuation-in-part of application No. 08/485,219, filed as application No. PCT/US94/05168 on May 10, 1994, now Pat. No. 5,697,281, which is a continuation-in-part of application No. 08/059,681, filed on May 10, 1993, now abandoned.

(51) Int. Cl.[7] ................................ A61M 31/00
(52) U.S. Cl. ............................. 604/500; 604/28
(58) Field of Search ............... 604/114, 22, 500, 604/28

(56) References Cited

U.S. PATENT DOCUMENTS

| | | | |
|---|---|---|---|
| 4,033,351 | * 7/1977 | Hetzel | 128/303 |
| 4,040,426 | * 8/1977 | Morrison, Jr. | 128/303 |

(List continued on next page.)

FOREIGN PATENT DOCUMENTS

| | | | | |
|---|---|---|---|---|
| 0703461 | * | 3/1996 | (EP) | G01R/27/02 |
| 0 740 926 A2 | * | 11/1996 | (EP) | A61B/17/39 |
| 0 754 437 | * | 1/1997 | (EP) | A61B/17/39 |
| 2308979 | * | 7/1997 | (GB) | A61B/17/39 |
| 2308980 | * | 7/1997 | (GB) | A61B/17/36 |
| 2308981 | * | 7/1997 | (GB) | A61B/17/39 |
| WO 90/07303 | * | 7/1990 | (WO) | A61B/17/39 |
| WO 92/21278 | * | 12/1992 | (WO) | A61B/5/04 |
| WO93/20747 | * | 10/1993 | (WO) | A61B/5/00 |
| WP94/03134 | * | 2/1994 | (WO) | A61F/9/00 |
| WO 94/26228 | * | 11/1994 | (WO) | A61G/17/36 |
| WO95/05780 | * | 3/1995 | (WO) | . |
| WO95/34259 | * | 12/1995 | (WO) | A61F/5/48 |
| WO 96/35469 | * | 11/1996 | (WO) | A61M/25/00 |
| WO 96/39962 | * | 12/1996 | (WO) | A61B/17/36 |
| WO 96/39964 | * | 12/1996 | (WO) | A61B/17/36 |
| WO 96/39965 | * | 12/1996 | (WO) | A61B/17/36 |
| WO 97/00646 | * | 1/1997 | (WO) | A61B/17/39 |
| WO97/00647 | * | 1/1997 | (WO) | A61B/17/39 |
| WO 97/24073 | * | 7/1997 | (WO) | A61B/17/39 |
| WO 97/24993 | * | 7/1997 | (WO) | A61B/17/39 |
| WO 97/24994 | * | 7/1997 | (WO) | A61B/17/39 |
| WO 97/48346 | * | 12/1997 | (WO) | A61B/17/39 |

OTHER PUBLICATIONS

Salter, L.F. (1996) *Catheterization and Cardiovascular Diagnosis* 37:320–321. "Remedies" for In–Stent Restenosis.*

(List continued on next page.)

Primary Examiner—Mike Thompson
Assistant Examiner—Sharon Kennedy
(74) Attorney, Agent, or Firm—John T. Raffle

(57) ABSTRACT

The present invention comprises apparatus and methods for maintaining patency in body passages subject to occlusion by invasive tissue growth. The apparatus and methods of the present invention may be used to open and maintain patency in virtually any hollow body passage which may be subject to occlusion by invasive cellular growth or invasive solid tumor growth. Suitable hollow body passages include ducts, orifices, lumens, and the like, with exemplary body passages including the coronary arteries. The present invention is particularly useful for reducing or eliminating the effects of restenosis in coronary arteries by selectively removing tissue ingrowth in or around stents anchored therein.

25 Claims, 12 Drawing Sheets

U.S. PATENT DOCUMENTS

| | | | |
|---|---|---|---|
| 4,043,342 | * 8/1977 | Morrison, Jr. | 128/303 |
| 4,116,198 | * 9/1978 | Roos | 128/303 |
| 4,202,337 | * 5/1980 | Hren et al. | 128/303 |
| 4,228,800 | * 10/1980 | Degler, Jr. et al. | 128/303 |
| 4,248,231 | * 2/1981 | Herczog et al. | 128/303 |
| 4,326,529 | * 4/1982 | Doss et al. | 128/303 |
| 4,381,007 | * 4/1983 | Doss | 128/303 |
| 4,476,862 | * 10/1984 | Pao | 128/303 |
| 4,532,924 | * 8/1985 | Auth et al. | 128/303.17 |
| 4,548,207 | * 10/1985 | Reimels | 128/303 |
| 4,582,056 | * 4/1986 | McCorkle, Jr. . | |
| 4,674,499 | * 6/1987 | Pao | 128/303 |
| 4,682,596 | * 7/1987 | Bales et al. | 128/303 |
| 4,706,667 | * 11/1987 | Roos | 128/303 |
| 4,709,698 | * 12/1987 | Johnston et al. | 128/303 |
| 4,765,331 | * 8/1988 | Petruzzi et al. | 128/303 |
| 4,799,479 | * 1/1989 | Spears . | |
| 4,823,791 | * 4/1989 | D'Amelio et al. | 123/303 |
| 4,860,752 | * 8/1989 | Turner | 128/422 |
| 4,907,586 | * 3/1990 | Bille et al. | 606/5 |
| 4,955,377 | * 9/1990 | Lennox et al. | 128/401 |
| 4,967,765 | * 11/1990 | Turner et al. | 128/785 |
| 4,976,709 | * 12/1990 | Sand | 606/5 |
| 4,976,711 | * 12/1990 | Parins et al. | 606/48 |
| 4,998,933 | * 3/1991 | Eggers et al. | 606/41 |
| 5,000,751 | * 3/1991 | Schroder et al. | 606/4 |
| 5,007,908 | * 4/1991 | Rydell | 606/47 |
| 5,009,656 | * 4/1991 | Reimels | 606/48 |
| 5,057,105 | * 10/1991 | Malone et al. | 606/28 |
| 5,057,106 | * 10/1991 | Kasevich et al. | 606/33 |
| 5,078,717 | * 1/1992 | Parins et al. | 606/48 |
| 5,078,736 | * 1/1992 | Behl . | |
| 5,083,565 | * 1/1992 | Parins et al. | 128/642 |
| 5,098,431 | * 3/1992 | Rydell | 606/48 |
| 5,108,391 | * 4/1992 | Flachenecker et al. | 606/38 |
| 5,122,138 | * 6/1992 | Manwaring | 606/46 |
| 5,125,928 | * 6/1992 | Parins et al. | 606/48 |
| 5,137,530 | * 8/1992 | Sand | 606/5 |
| 5,140,987 | * 8/1992 | Schuger et al. . | |
| 5,152,759 | * 10/1992 | Parel et al. | 606/5 |
| 5,178,618 | * 1/1993 | Kandarpa . | |
| 5,178,620 | * 1/1993 | Eggers et al. . | |
| 5,190,517 | * 3/1993 | Zieve et al. | 604/22 |
| 5,190,540 | * 3/1993 | Lee . | |
| 5,195,959 | * 3/1993 | Smith | 604/34 |
| 5,197,963 | * 3/1993 | Parins | 606/46 |
| 5,217,457 | * 6/1993 | Delahuerga et al. | 606/42 |
| 5,222,938 | * 6/1993 | Behl . | |
| 5,224,953 | * 7/1993 | Morgentaler . | |
| 5,230,334 | * 7/1993 | Klopotek | 128/399 |
| 5,246,438 | * 9/1993 | Langberg | 606/33 |
| 5,250,045 | * 10/1993 | Bohley . | |
| 5,263,951 | * 11/1993 | Spears et al. | 606/12 |
| 5,267,994 | * 12/1993 | Gentelia et al. | 606/15 |
| 5,267,997 | * 12/1993 | Farin et al. | 606/38 |
| 5,273,524 | * 12/1993 | Fox et al. | 604/21 |
| 5,281,211 | * 1/1994 | Parel et al. | 606/5 |
| 5,281,216 | * 1/1994 | Klicek | 606/42 |
| 5,281,218 | * 1/1994 | Imran | 606/41 |
| 5,290,282 | * 3/1994 | Casscells | 606/29 |
| 5,292,321 | * 3/1994 | Lee . | |
| 5,300,069 | * 4/1994 | Hunsberger et al. | 606/37 |
| 5,312,400 | * 5/1994 | Bales et al. | 606/41 |
| 5,314,406 | * 5/1994 | Arias et al. | 604/21 |
| 5,330,470 | * 7/1994 | Hagen | 606/42 |
| 5,334,190 | * 8/1994 | Seiler | 606/5 |
| 5,342,357 | * 8/1994 | Nardella | 606/40 |
| 5,348,553 | * 9/1994 | Whitney . | |
| 5,366,443 | * 11/1994 | Eggers et al. | 604/114 |
| 5,370,675 | * 12/1994 | Edwards et al. | 607/101 |
| 5,374,265 | * 12/1994 | Sand | 606/5 |
| 5,380,277 | * 1/1995 | Phillips | 604/33 |
| 5,380,316 | * 1/1995 | Aita et al. . | |
| 5,383,917 | * 1/1995 | Desai et al. | 607/702 |
| 5,389,096 | * 2/1995 | Aita et al. . | |
| 5,395,312 | * 3/1995 | Desai | 604/22 |
| 5,400,428 | * 3/1995 | Grace . | |
| 5,417,687 | * 5/1995 | Nardella et al. | 606/32 |
| 5,419,767 | * 5/1995 | Eggers et al. | 604/114 |
| 5,423,806 | * 6/1995 | Dale et al. . | |
| 5,423,882 | * 6/1995 | Jackman et al. | 607/122 |
| 5,425,355 | * 6/1995 | Kulick | 128/4 |
| 5,429,604 | * 7/1995 | Hammersmark et al. . | |
| 5,433,708 | * 7/1995 | Nichols et al. . | |
| 5,437,658 | * 8/1995 | Muller et al. | 606/5 |
| 5,454,809 | * 10/1995 | Janssen | 606/41 |
| 5,456,680 | * 10/1995 | Taylor et al. . | |
| 5,484,433 | * 1/1996 | Taylor et al. . | |
| 5,505,725 | * 4/1996 | Samson . | |
| 5,507,771 | * 4/1996 | Gianturco . | |
| 5,514,128 | * 5/1996 | Hillsman et al. . | |
| 5,540,712 | * 7/1996 | Kleshinski et al. . | |
| 5,542,928 | * 8/1996 | Evans et al. . | |
| 5,545,161 | * 8/1996 | Imran | 606/41 |
| 5,545,211 | * 8/1996 | An et al. . | |
| 5,554,152 | * 9/1996 | Aita et al. . | |
| 5,567,890 | * 10/1996 | Ohta et al. | 128/303 |
| 5,569,242 | * 10/1996 | Lax et al. | 606/42 |
| 5,571,169 | * 11/1996 | Plaia et al. . | |
| 5,579,764 | * 12/1996 | Goldreyer | 128/642 |
| 5,603,731 | * 2/1997 | Whitney . | |
| 5,609,151 | * 3/1997 | Mulier et al. | 128/642 |
| 5,620,438 | * 4/1997 | Amplatz et al. . | |
| 5,643,251 | * 7/1997 | Hillsman et al. . | |
| 5,643,255 | * 7/1997 | Organ | 606/41 |
| 5,647,869 | * 7/1997 | Goble et al. | 606/37 |
| 5,681,282 | * 10/1997 | Eggers et al. | 604/114 |
| 5,683,366 | * 11/1997 | Eggers et al. . | |
| 5,697,281 | * 12/1997 | Eggers et al. . | |
| 5,697,536 | * 12/1997 | Eggers et al. . | |
| 5,697,882 | * 12/1997 | Eggers et al. . | |
| 5,697,909 | * 12/1997 | Eggers et al. . | |
| 5,700,262 | * 12/1997 | Acosta | 606/48 |
| 5,725,524 | * 3/1998 | Mulier et al. | 606/41 |
| 5,749,914 | * 5/1998 | Janssen . | |
| 5,766,153 | * 6/1998 | Eggers et al. | 604/114 |
| 5,766,192 | * 6/1998 | Zacca | 606/159 |
| 5,775,338 | * 7/1998 | Hastings | 128/898 |
| 5,810,764 | | 9/1998 | Eggers et al. . |
| 5,843,019 | | 12/1998 | Eggers et al. . |
| 5,860,951 | | 1/1999 | Eggers et al. . |
| 5,871,469 | | 2/1999 | Eggers et al. . |
| 5,873,855 | | 2/1999 | Eggers et al. . |
| 5,888,198 | | 3/1999 | Eggers et al. . |
| 5,891,095 | | 4/1999 | Eggers et al. . |
| 5,902,272 | | 5/1999 | Eggers et al. . |
| 5,944,715 | | 8/1999 | Goble et al. . |

OTHER PUBLICATIONS

Topaz, O., et al. (1996) *Catheterization and Cardiovascular Diagnosis* 37:293–299. The Stenotic Stent: Mechanisms and Revascularization Options.*

V.E. Elsasser et al. *Acta Medicotechnica* vol. 24, No. 4, pp. 129–134 (1976).*

P.C. Nardella (1989) *SPIE* 1068:42–49 Radio Frequency Energy and Impedance Feedback.*

Rand et al. (1985) *J. Arthro. Surg.* 1:242–246 Effect of Electrocautery on Fresh Human Articular Cartilage.*

* cited by examiner

SYSTEM AND METHODS FOR ELECTROSURGICAL RESTENOSIS OF BODY LUMENS

CROSS-REFERENCE TO RELATED APPLICATIONS

The present invention is a continuation-in-part of commonly-assigned applications Ser. No. 08/561,958, filed on Nov. 22, 1995, now U.S. Pat. No. 5,697,882; which is a continuation-in-part of Ser. No. 08/485,219, filed on Jun. 7, 1995 now U.S. Pat. No. 5,697,281; PCT International Application, U.S. National Phase Serial No. PCT/US94/05168, filed on May 10, 1994; Ser. No. 08/059,681, filed on May 10, 1993, abandoned, the full disclosures of which are incorporated herein by reference for all purposes.

BACKGROUND OF THE INVENTION

Field of the Invention

The present invention relates generally to apparatus and methods for maintaining patency in body passages and more particularly to a catheter system capable of selectively ablating occlusive media within a body lumen. The present invention is particularly useful for the electrosurgical cutting or ablation of invasive tissue growth in and around a stent anchored in the body lumen to help reduce or eliminate restenosis of the body lumen.

When a patient is suffering from atherosclerosis, significant occlusions or blockages are formed on the interior wall of the artery. As a result of these occlusions, the organ or extremity to which blood is to be supplied is compromised and the patient may experience a myocardial infarction or stroke. In less severe cases, it is often sufficient to treat the symptoms with pharmaceuticals and lifestyle modification to lessen the underlying causes of the disease. In more severe cases, a coronary artery blockage can often be treated using endovascular techniques such as balloon angioplasty, atherectomy, laser or hot tip ablation, placement of stents, and the like.

Percutaneous transluminal balloon angioplasty (PTBA) has become a recognized method of reducing the occlusion of blood vessels. The procedure involves routing a catheter having an inflatable balloon at the distal end thereof through the vascular system until the balloon is positioned at the site of the stenotic lesion to be treated. The balloon is then inflated to compress the atherosclerotic plaque into the wall of the blood vessel, thus increasing the size of the opening and enhancing blood flow through the affected artery. However, this successful procedure is overshadowed by the occurrence of restenosis, a re-narrowing of the artery. Studies have shown that 30–40 percent of angioplasty patients experience restenosis within 3–6 months of the angioplasty procedure. When restenosis occurs, patients may be treated with cardiovascular medications, additional angioplasty procedures or bypass surgery.

Restenosis often occurs because the wall of the dilated artery tends to spring back to its original shape following deflation of the dilation balloon. Arterial stenting has been introduced as a solution to the recoil of the vessel wall. Arterial stenting involves the placement of an expandable coil spring or wire-mesh tube within the occluded artery to reopen the lumen of the blood vessel. One example of an arterial stent is disclosed in U.S. Pat. No. 4,739,792 to Julio Palmaz. The Palmaz device comprises an expandable wire-mesh graft or prosthesis which is mounted upon an inflatable balloon catheter. The catheter assembly, including the graft, is delivered to the occluded area and is then inflated to radially force the graft into contact with the occlusion. As the graft expands, the lumen of the blood vessel is opened and blood flow is restored. After complete expansion of the graft, the balloon catheter is deflated and removed, leaving behind the graft to buttress and prevent elastic recoil of the blood vessel wall.

Although this method is successful in preventing recoil of the vessel wall, restenosis will often still occur. Smooth muscle cells which form the vessel wall tend to proliferate and build-up in the newly stented area of the blood vessel. This cellular build-up may eventually become large enough to block the lumen of the blood vessel.

It has recently been determined that localized heating of the blood vessel wall may inhibit the proliferation of smooth muscle cells which are believed to cause restenosis. One example of localized blood vessel heating is disclosed in U.S. Pat. No. 4,799,479 to Spears. The Spears patent discloses an apparatus for angioplasty having an inflatable balloon catheter which is provided with a meshwork of electrical wires to supply heat to a vessel wall. Following balloon angioplasty, the external surface of the balloon is heated to fuse together disrupted tissue elements and to kill smooth muscle cells which are believed to lead to restenosis. Unfortunately, the Spears device does not adequately prevent the spontaneous elastic recoil of the arterial wall. Immediately following angioplasty, the arterial wall begins to spring back to its original shape.

Thus stenting in and of itself is ineffective in preventing restenosis due to the occurrence of cellular proliferation. Likewise, balloon dilation in combination with localized heating does not adequately prevent restenosis since the vessel wall tends to spontaneously return to its original occluded shape.

Other techniques have recently been developed to help reduce incidences of restenosis. For example, procedures for irradiating the angioplasty site with UV light to reduce the proliferation of smooth muscle cells at the site have been disclosed. In addition, techniques have been disclosed for the controlled application of thermal and/or electrical energy directly to the stent by, for example, including resistive or inductive heating elements that may include radiofrequency electrodes within the stent. The radiofrequency energy is then applied to the stent to disrupt the cellular growth in or around the stent. One major disadvantage of these procedures is that it is difficult to selectively apply the energy to the invasive tissue without causing thermal damage to the body lumen wall. In particular, methods that apply energy, such as RF energy, directly to the stent will often cause thermal damage to the surrounding body lumen in which the stent is anchored.

SUMMARY OF THE INVENTION

The present invention comprises apparatus and methods for maintaining patency in body passages subject to occlusion by invasive tissue growth. The apparatus and methods of the present invention may be used to open and maintain patency in virtually any hollow body passage which may be subject to occlusion by invasive cellular growth or invasive solid tumor growth. Suitable hollow body passages include ducts, orifices, lumens, and the like, with exemplary body passages including the coronary arteries. The present invention is particularly useful for reducing or eliminating the effects of restenosis in coronary arteries by selectively removing tissue ingrowth in or around stents anchored therein.

The principles of the present invention are generally applicable to any body lumen which becomes partially or totally occluded. The present invention is particularly useful in a lumen containing a lumenal prosthesis, such as a stent, stent-graft or graft, which may be metallic, nonmetallic or a non-metallic coated metallic structure.

Restenosis often occurs when arthermateous media or thrombus moves or grows through or around the cylindrical wall of the prosthesis to partially occlude the body passage. Methods of the present invention comprise advancing an electrosurgical catheter within the body passage such that an electrode terminal is positioned near the occlusive media. High frequency voltage is applied to one or more electrode terminal(s) at the distal end of the catheter such that an electrical current flows from the electrode terminal(s), through the region of the occlusive media and to the return electrode to selectively remove the occlusive media without directly applying thermal or electrical energy to the prothesis or the lumenal wall. The electrode terminal is then advanced through the vacancy left by the removed occlusive media to recanalize the vessel. By selectively removing the occlusive media without passing energy directly to the stent, thermal damage to the surrounding lumenal wall is minimized.

A particular advantage of the present invention is the confinement of current flow paths between the return electrode and one or more electrode terminals to the vicinity of tissue ablating region. This confinement of current flow paths minimizes the undesired flow of current through portions or all of the stent, which may otherwise induce non-specific tissue injury beyond the site of recanalization of the occluded lumen. In one configuration, the return electrode is a movable guide wire positioned radially inward from the electrode terminal such that the electrical current flows from the electrode terminal radially inward to the return electrode, thereby inhibiting current flow through the prosthesis. In another embodiment, the return electrode is an annular band positioned proximal of the electrode terminal(s).

In preferred embodiments, the high frequency voltage is applied in the presence of electrically conducting fluid such that a current flow path is generated between the electrode terminal(s) and the return electrode through the electrically conducting fluid. Preferably, the electrically conductive fluid is delivered through an internal lumen in the catheter (or through a separate instrument) to a region around the occlusive media to displace naturally occurring bodily fluids. This region is then fluidly isolated to confine the electrically conducting fluid around the tissue ablation site.

In one embodiment, the region is isolated by advancing proximal and distal balloons to either side of the region, and inflating these balloons to effect a seal with the interior wall of the body passage.

Once the target site is isolated from the rest of the vasculature, the supply of electrically conductive fluid is continuously delivered to the region and balanced with the aspiration of fluid from the site of intended recanalization. The electrode terminal(s) are energized by applying a high frequency voltage between electrode terminal(s) and the return electrode, which can be a movable guide wire. A high electric field is created at the surface of the electrode(s) which causes the volumetric removal or ablation or target tissue in close proximity with the electrode terminal(s). As the occlusive media is ablated, gaseous products are generated which are entrained in the electrically conducting fluid and removed through the aspiration lumen in the catheter. The current flux lines are generally confined to the central portion of tissue ablation region because they generally flow inward towards the return electrode and because the occlusive media generally shields the outer region of the body passage (including the stent) from the current flux lines. This minimizes undesirable interaction between the electrical current and the stent. In an exemplary embodiment, the distal portion of the catheter body is reciprocally rotated as the electrode terminal is energized to selectively ablate the occlusive media. The catheter body is then advanced through the vacancy left by the ablated occlusive media to recanalize the vessel.

In a specific aspect of the invention, the high frequency voltage applied between the electrode terminal(s) and the return electrode generates high voltage gradients in the vicinity of the electrode terminals. These high voltage gradients are sufficient to create an electric field at the distal boundary of these electrodes(s) that is sufficiently high to break down the occlusive media through molecular dissociation or disintegration. The high frequency voltage imparts energy to the target site to ablate a thin layer of tissue without causing substantial tissue necrosis beyond the boundary of the occlusive media within the body passage. This ablative process can be precisely controlled to effect the volumetric removal of the occlusive media within a small blood vessel with minimal heating of, or damage to, the surrounding stent and lumenal wall.

A further understanding of the nature and advantages of the invention will become apparent by reference to the remaining portions of the specification and drawings.

DESCRIPTION OF THE PREFERRED EMBODIMENT

Figure 1:
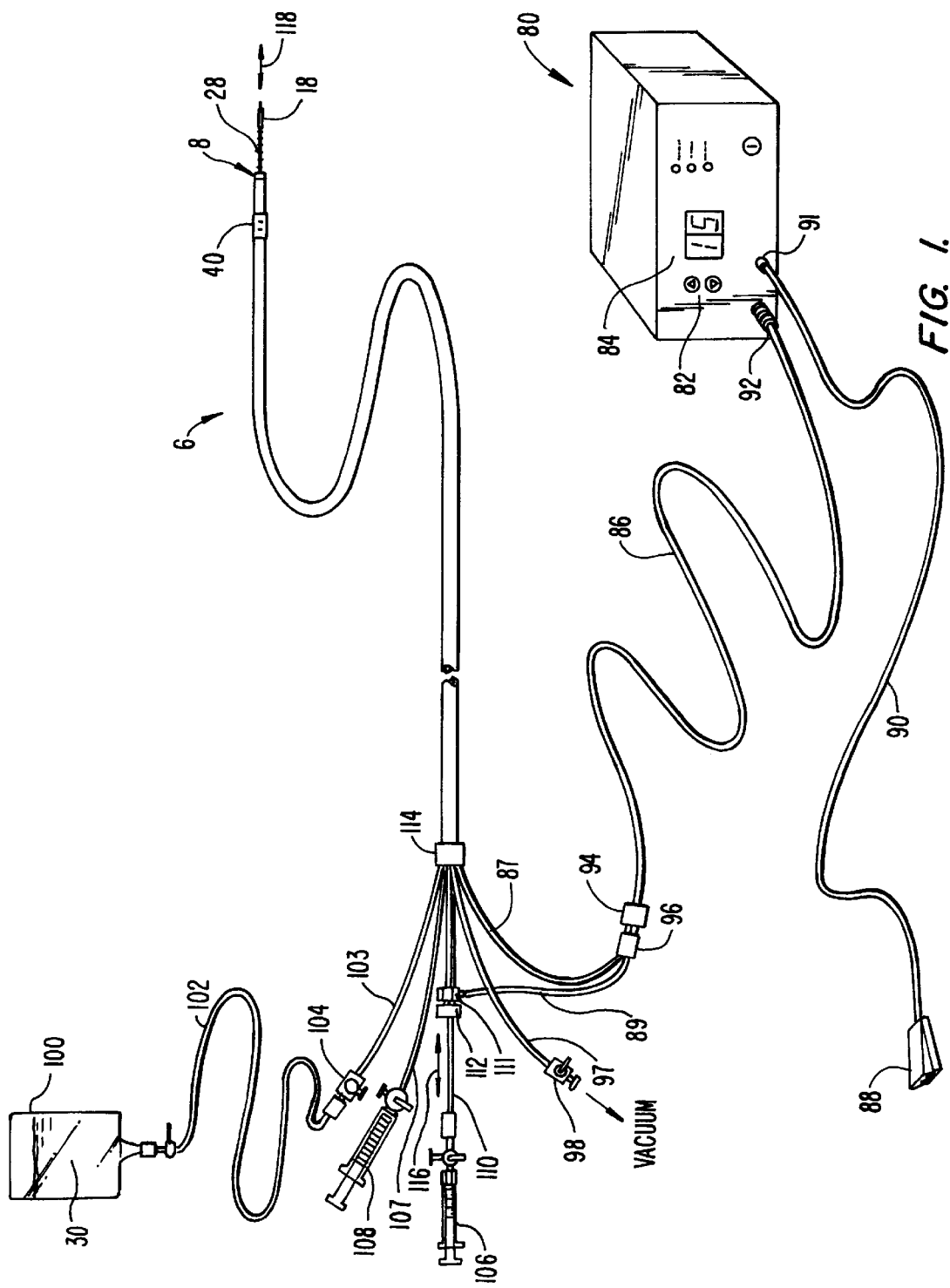
FIG. 1 schematically illustrates a lumen recanalization catheter system according to the present invention.

The present invention provides systems and methods for selectively applying electrical energy to a target location within or on a body lumen, particularly including atheromatous material which partially or fully occludes a blood vessel or other body lumen. In addition to blood vessels, body lumens that may be treated by the method and apparatus of the present invention include the urinary tract (which for example may be occluded by an enlarged prostrate in males), the fallopian tubes (which may be occluded and cause infertility), and the like. Exemplary solid tissues include abdominal tissues, neurological tissues, benign and malignant solid tumors, myocardial tissue and the like. Thus, the methods and apparatus may be used in a wide variety of procedures, including intravascular, urological, laparoscopic, arthroscopic, thoracoscopic, orthopedic, gynecologic, electrothermal, lithotripsy, spinal disc ablation, and the like. For convenience, the remaining disclosure will be directed specifically to the intravascular treatment of blood vessels but it should be appreciated that the apparatus and methods can be applied to other body lumens and passages as well as solid tissue sites for a variety of purposes.

The stenotic material in blood vessels will be, by way of example but not limited to, atheroma or atheromatous plaque. It may be relatively soft (fresh) or it may be calcified and hardened. The invention applies heat selectively to the stenotic material while limiting unwanted heating of the blood, the surrounding vessel wall and the stent anchored therein. More particularly, the present invention confines the current flow paths between the return electrode and electrode terminals to the vicinity of the tissue ablating region. This confinement of current flow paths minimizes the undesired flow of current through portions or all of the stent, which may otherwise induce non-specific tissue injury beyond the site of recanalization of the occluded lumen.

The present invention may use a single active electrode or an electrode array distributed over a distal contact surface of a catheter. The electrode array usually includes a plurality of independently current-limited and/or power-controlled electrode terminals to apply electrical energy selectively to the target tissue while limiting the unwanted application of electrical energy to the surrounding tissue and environment (e.g., the stent and the lumenal wall). The electrode terminals may be independently current-limited by isolating the terminals from each other and connecting each terminal to a separate power source or current or power limiting element (e.g., inductor) that is isolated from the other electrode terminals. Alternatively, the electrode terminals may be connected to each other at either the proximal or distal ends of the probe to form a single wire that couples to a power source.

The electrosurgical catheter will comprise a flexible body having a proximal end and a distal end which supports one or more electrode terminals. The electrode terminal(s) are preferably supported by an inorganic insulating support positioned near the distal end of the catheter body. The return electrode may be part of the catheter body, part of a separate movable guide wire or on another instrument. In the preferred embodiments, the return electrode comprises a separate movable guide wire positioned within an internal lumen of the catheter body. The proximal end of the catheter will include the appropriate electrical connections for coupling the return electrode and the electrode terminal(s) to a high frequency power supply, such as an electrosurgical generator.

The catheter will also include other internal lumens for providing separate functions, such as delivering fluid and aspirating products of ablation from the target site. Preferably, the catheter will have a fluid delivery lumen for delivering electrically conducting fluid to the target site, and an aspiration lumen coupled to a vacuum source for aspirating non-condensible gases and other products of ablation from the site.

The catheter will also preferably include an isolation system for fluidly isolating the region around the target site. In one embodiment, the isolation system includes proximal and distal balloons that are movable to portions of the body passage proximal and distal to the region of the target site. The distal balloon, by way of example, may be formed on a hollow guide wire that is fluidly coupled to an inflation source, such as a syringe. The proximal balloon, for example, may be coupled to the catheter body proximal to the active and return electrodes.

The invention typically includes guiding apparatus for guiding the catheter along a pathway approximating the central region of the occluded blood vessel. The guiding apparatus is usually an electrically conducting wire that may serve as the return electrode. The electrically conducting wire is extensible from the tip of the catheter and is located within and concentric to the catheter conveniently being in the form of a movable or fixed guidewire, usually being a movable guidewire.

The electrode array may include only one electrode terminal, or it may include at least two isolated electrode terminals, sometimes at least four electrode terminals, sometimes at least six electrode terminals, and often 50 or more electrode terminals, disposed over the distal contact surfaces on the catheter. By bringing the electrode array(s) on the contact surface(s) in close proximity with the target tissue (e.g., occlusive media) and applying high frequency voltage between the array(s) and an additional return electrode in direct or indirect contact with the patient's body, the target tissue is selectively ablated or cut, permitting selective removal of portions of the target tissue while desirably minimizing the application of energy to the surrounding stent and lumenal wall.

In an exemplary embodiment, each individual electrode terminal in the electrode array is electrically insulated from all other electrode terminals in the array and is connected to a power source which is isolated from each of the other electrodes in the array or to circuitry which limits or interrupts current flow to the electrode when low resistivity material (e.g., blood or electrically conductive saline irrigant) causes a lower impedance path between the return electrode and the individual electrode terminal. The isolated power sources for each individual electrode may be separate power supply circuits having internal impedance characteristics which limit power to the associated electrode terminal when a low impedance return path is encountered, may be a single power source which is connected to each of the electrodes through independently actuatable switches or may be provided by independent current or power limiting elements, such as inductors, capacitors, resistors and/or combinations thereof. The current or power limiting elements may be provided in the probe, connectors, cable, controller or along the conductive path from the controller to the distal tip. A more complete description of a system and method for selectively limiting current and power to an array of isolated electrode terminals can be found in commonly assigned, copending application Ser. No. 08/561,958, filed Nov. 22, 1995 (attorney docket No. 16238-000700), the complete disclosure of which is incorporated herein by reference for all purposes.

In a preferred aspect, this invention takes advantage of the differences in electrical resistivity between the target occlusive media and the surrounding conductive liquid (e.g., isotonic saline irrigant, blood or the like). By way of example, for any selected level of applied voltage, if the electrical conduction path between the return electrode and one of the individual electrode terminals within the electrode array is blood (having a relatively low electrical impedance), the current control means connected to the individual electrode will limit current flow so that the heating of intervening conductive fluid is minimized. On the other hand, if a portion of or all of the electrical conduction path between the common or return electrode and one of the individual electrode terminals within the electrode array is occlusive media (having a relatively higher electrical impedance), the current control circuitry or switch connected to the individual electrode will allow current flow sufficient for the deposition of electrical energy and associated ablation or electrical breakdown of the target tissue in the immediate vicinity of the electrode surface.

It should be clearly understood that the invention is not limited to electrically isolated electrode terminals, or even to a plurality of electrode terminals. For example, the array of active electrode terminals may be connected to a single lead that extends through the catheter shaft to a power source of high frequency current. Alternatively, the catheter may incorporate a single electrode that extends directly through the catheter shaft or is connected to a single lead that extends to the power source.

In the case of a single electrode, the invention may also use current limiting means to apply electrical energy selectively to the target tissue while limiting the unwanted application of electrical energy to the surrounding tissue. In this embodiment, the electrode may be connected to current limiting elements or to circuitry which limits or interrupts current flow to the electrode when low resistivity material (e.g., blood or electrically conductive saline irrigant) causes a lower impedance path between the return electrode and the electrode. The current limiting elements or circuitry may be configured to completely interrupt or modulate current flow to the electrode, for example, when a certain percentage of the electrode surface is in contact with low resistivity material. In one embodiment, the current flow will be modulated or completely interrupted when, for example, a large portion of the electrode surface is exposed to electrically conductive fluids and, therefore, not in sufficiently close proximity or contact with the target tissue. In this manner, current can be selectively applied to the target tissue, while minimizing current flow to surrounding fluids and adjacent non-target tissue structures.

In addition to the above described methods, the applicant has discovered another mechanism for ablating tissue while minimizing the depth of necrosis. This mechanism involves applying a high frequency voltage between the active electrode surface and the return electrode to develop high electric field intensities in the vicinity of the target tissue site. In this embodiment, the active electrode(s) include at least one active portion having a surface geometry configured to promote substantially high electric field intensities between the active portion and the target site when a high frequency voltage is applied to the electrodes. These high electric field intensities are sufficient to break down the tissue by processes including molecular dissociation or disintegration. The high frequency voltage imparts energy to the target site to ablate a thin layer of tissue without causing substantial tissue necrosis beyond the boundary of the thin layer of tissue ablated. This ablative process can be precisely controlled to effect the volumetric removal of tissue with minimal heating of or damage to the surrounding stent and tissue structures, such as the lumenal wall.

In an exemplary embodiment, the high electric field intensities at the active portion of the active electrode(s) may be generated by positioning the active electrode and target site within an electrically conducting fluid, such as isotonic saline or the naturally occurring body fluids in a blood vessel, such as blood, and applying a high frequency voltage that is sufficient to vaporize the electrically conducting fluid over at least a portion of the surface of the active electrode in the region between the active portion of the active electrode and the target tissue. Since the vapor layer or vaporized region has a relatively high electrical impedance, it increases the voltage differential between the active electrode tip and the tissue and causes ionization within the vapor layer due to the presence of an ionizable species (e.g., sodium when isotonic saline is the electrically conducting fluid). This ionization, under optimal conditions, induces the discharge of energetic electrons and photons from the vapor layer and to the surface of the target tissue. A more detailed description of this phenomena can be found in application Ser. No. 08/561,958, filed on Nov. 22, 1995 (Attorney Docket 16238-000700), the complete disclosure of which has already been incorporated herein by reference.

Suitable electrode surface geometries for producing sufficiently high electric field intensities to reach the threshold conditions for vapor layer formation may be obtained by producing sharp edges, discontinuities, and/or corners at the active portion of the active electrode(s). Alternatively, the electrode(s) may be specifically designed to increase the edge/surface area ratio of the active portion through the use of shaped wires (e.g., square or hexagonal wires) or tubular electrodes offering high electric field intensities along the inside and outside perimeters of the tubular electrode. Additionally or alternatively, the active electrode surface(s) may be modified through chemical, electrochemical or abrasive methods to create a multiplicity of surface aspirates on the electrode surface. Suitable electrode designs for use with the present invention may be found in co-pending, commonly assigned application Ser. No. 08/687,792, filed Jul. 19, 1996 (Attorney Docket No. 16238-16), the complete disclosure of which is incorporated herein by reference.

The voltage applied between the return electrode and the electrode array will be at high or radio frequency, typically between about 5 kHz and 20 MHz, usually being between about 30 kHz and 2.5 MHz, and preferably being between about 50 kHz and 1 MHz. The RMS (root mean square) voltage applied will usually be in the range from about 5 volts to 1000 volts, preferably being in the range from about 50 volts to 800 volts, and more preferably being in the range from about 60 volts to 500 volts. These frequencies and voltages will result in peak-to-peak voltages and current that are sufficient to vaporize the electrically conductive fluid and, in turn, create the conditions within the vaporized region which result in high electric fields and emission of energetic photons and/or electrons to ablate tissue. Typically, the peak-to-peak voltage will be in the range of 40 to 4000 volts and preferably in the range of 100 to 3200 volts and more preferably in the range of 300 to 2400 volts.

As discussed above, the voltage is usually delivered in a waveform having a sufficiently high frequency (e.g., on the order of 5 kHz to 20 MHz) such that the voltage is effectively applied continuously (as compared with e.g., lasers claiming small depths of necrosis, which are generally delivered in brief pulses at a repetition rate of about 10 to 20 Hz). Hence, the duty cycle (i.e., cumulative time in any one-second interval that energy is applied) is on the order of about 50% for the present invention, as compared with lasers which typically have a duty cycle of about 0.001% to 0.0001%.

Usually, the current level will be selectively limited or controlled and the voltage applied will be independently adjustable, frequently in response to the resistance of tissues and/or fluids in the pathway between an individual electrode and the return electrode. Also, the applied voltage level may be in response to a temperature control means which maintains the target tissue temperature within desired limits at the interface between the electrode arrays and the target tissue. The desired tissue temperature along a propagating surface just beyond the region of ablation will usually be in the range from about 40° C. to 100° C., and more usually from about 50° C. to 60° C. The tissue being ablated (and hence removed from the operation site) immediately adjacent the electrode array may reach even higher temperatures. A temperature sensor may be incorporated within the distal end of the electrosurgical device to measure a temperature indicative of the nearby tissue beyond the ablation boundary.

Referring to the drawings in detail, wherein like numerals indicate like elements, a lumen recanalization catheter system 2 is shown constructed according to the principles of the present invention. Catheter system 2 generally comprises an electrosurgical catheter 6 connected to a power supply 80 by an interconnecting cable 86 for providing high frequency voltage to a target tissue and an irrigant reservoir or source 100 for providing electrically conducting fluid to the target site. Catheter 6 generally comprises an elongate, flexible shaft body 12 including a tissue ablating region 8 at the distal end of body 12, and a proximal balloon 40 positioned on body 12 proximal to region 8. In a specific embodiment, a guide wire 28 (which may also serve as a return electrode) includes a distal balloon 18 which may be axially translated relative to region 8 and proximal balloon 40, as discussed in further detail below.

The proximal portion of catheter 6 includes a multi-lumen fitment 114 which provides for interconnections between lumens and electrical leads within catheter 6 and conduits and cables proximal to fitment 114. By way of example, a catheter electrical connector 96 is removably connected to a distal cable connector 94 which, in turn, is removably connectable to generator 80 through connector 92. One or more electrically conducting lead wires (not shown) within catheter 6 extend between one or more active electrodes at tissue ablating region 8 and one or more corresponding electrical terminals (also not shown) in catheter connector 96 via active electrode cable branch 87. In the illustrative embodiment, hollow guide wire 28 functions as the return electrode, and is electrically attached within a contact housing 111 by a sliding electrical contact (not shown). A return electrode cable branch 89 couples the sliding electrical contact to catheter connector 96. Electrical leads within cable 86 allow connection between terminals corresponding to return electrode 28 and one or more active electrodes 32 in distal cable connector 94 and generator 80.

Generator 80 is a high frequency generator operating at a frequency in the range of about 5 kHz to 20 MHZ, more preferably in the range of 30 kHz to 2.5 MHZ. The output voltage of generator 80 can be selectively applied between the return electrode and one or more active electrodes using footpedal 88, which is coupled to generator 80 via a footpedal cable 90 and removable connector 91. Generator has a selector 84 to change the applied voltage level, and may also include a second pedal (not shown) for remotely adjusting the energy level applied to the electrodes. A more complete description of a suitable generator is described in commonly assigned copending patent application Ser. No. 08/561,958, filed Nov. 22, 1995, (attorney docket no. 16238-000700), the complete disclosure of which has previously been incorporated herein by reference.

Conductive fluid 30 is provided to tissue ablation region 8 of catheter 6 via a lumen (not shown in FIG. 1) within catheter 6. Fluid is supplied to lumen from the source along a conductive fluid supply line 102 and a conduit 103, which is coupled to the inner catheter lumen at multi-lumen fitment 114. The source of conductive fluid (e.g., isotonic saline) may be an irrigant pump system (not shown) or a simple gravity-driven supply, such as an irrigant reservoir 100 positioned several feet above the level of the patient and tissue ablating region 8. A control valve 104 may be positioned at the interface of fluid supply line 102 and conduit 103 to allow manual control of the flow rate of electrically conductive fluid 30. Alternatively, a metering pump or flow regulator may be used to precisely control the flow rate of the conductive fluid.

System 2 further includes an aspiration or vacuum system (not shown) to aspirate liquids and gases from the target site, and syringes 106, 108 for inflating distal and proximal balloons 18, 40, respectively. By way of example, as the plunger of syringe 108 is depressed, fluid in the syringe chamber is displaced such that it flows through a conduit 107 and an internal lumen 57 within catheter 6(not shown in FIG. 1) to expand and inflate balloon 40. Likewise, syringe 106 is provided at the proximal end of guide wire 28 for inflating distal balloon 18, as shown by translation vectors 116, 118. Also, guidewire 28 can be advanced or retracted relative to tissue ablation region 8 of catheter 6 as shown by translation vectors 116, 118 such that, for each increment of relative displacement 116 at the proximal end of catheter 6, there is a corrresponding displacement 118 of the hollow guidewire 28 relative to the tissue ablating region 8 of catheter 6.

Figure 2A:
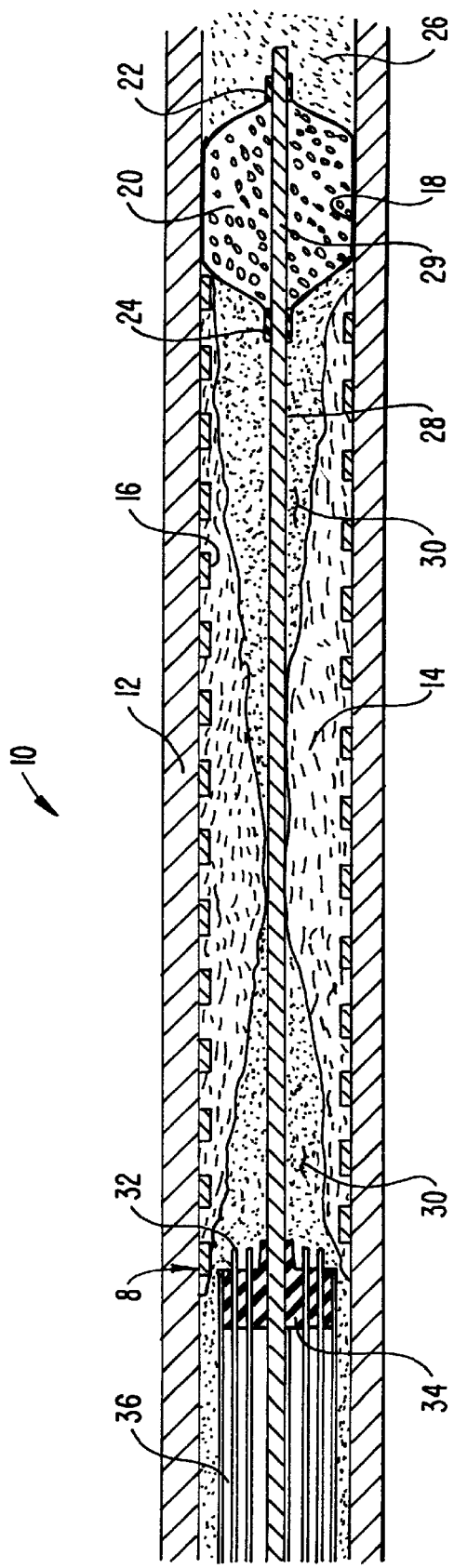
FIGS. 2A–2C illustrate a method of recanalizing an obstructed lumen according to the present invention.
Figure 2B:
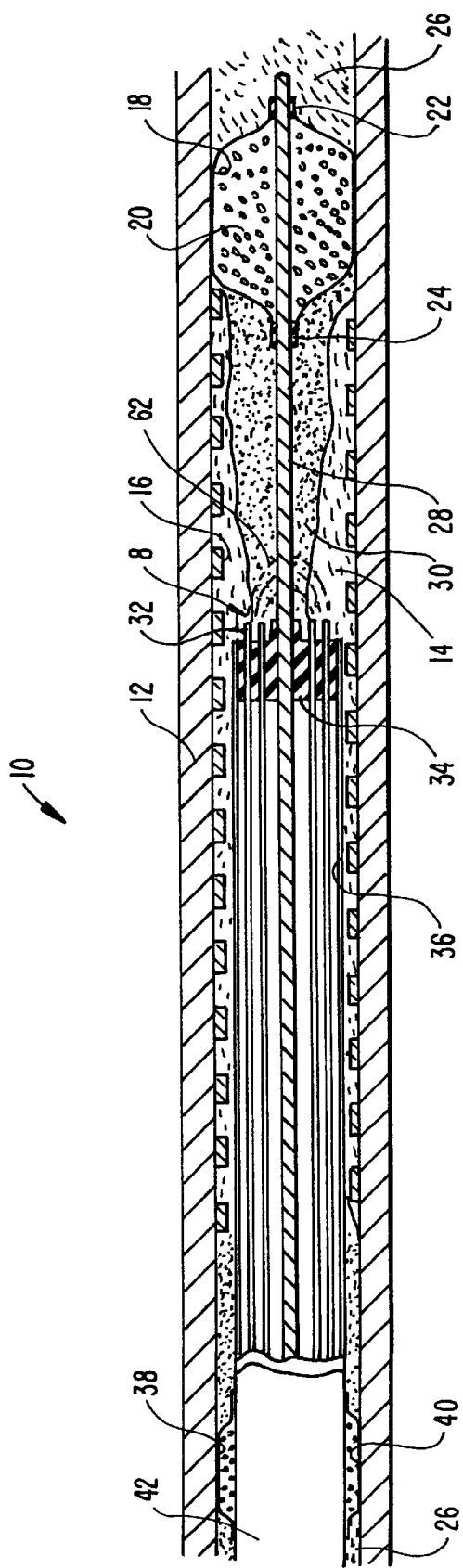
Figure 2C:
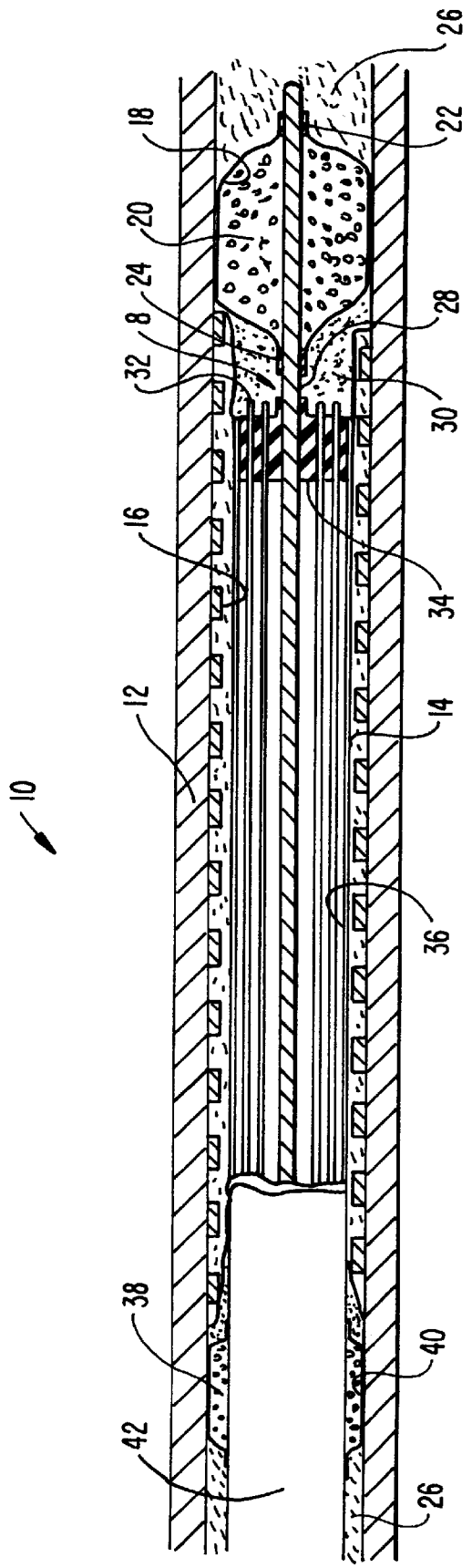

Referring now to FIGS. 2A–2C, one embodiment of the method and apparatus of the present invention will be described in detail. As shown, tissue ablating region 8 of catheter 6 progresses through occlusive media 14, such as athermateous media or thrombus within a body lumen 10, e.g., a blood vessel. The principles of the present invention are also applicable to any body lumen which becomes partially or totally occluded. The present invention is particularly useful in a lumen containing a lumenal prosthesis, such as a stent 16, stent-graft or graft, which may be metallic, nonmetallic or a non-metallic coated metallic structure. A particular advantage of the present invention is the confinement of current flow paths (not shown) between the return electrode (hollow guide wire 28 in the present example) and one or more active electrodes 32 to the vicinity of tissue ablating region 8. This confinement of current flow paths minimizes the undesired flow of current through portions or all of stent 16, which may otherwise induce non-specific tissue injury beyond the site of recanalization of the occluded lumen 10.

Referring to FIG. 2A, tissue ablating region 8 of catheter 6 is positioned proximal to the occlusive media 14 within lumen 10. The distal region of hollow guide wire 28 is positioned distal to the occlusive media 14 either before or after the initial positioning of tissue ablation region 8. Once hollow guide wire 28 is positioned as shown in FIG. 2A, proximal balloon 40 (not shown in FIG. 2A) is inflated to effect a seal between catheter shaft 42 and interior wall 12 of lumen 10 to minimize the flow of bodily fluid 26 (e.g., blood) from regions proximal to the tissue ablating region 8 of catheter 6. Electrically conductive and biologically compatible fluid 30 (e.g., isotonic saline) is delivered into lumen 10 for a sufficient period of time to displace naturally occurring bodily fluid 26 in the region between the tissue ablating region and the distal tip of guide wire 28. After the bodily fluid has been displaced, distal balloon 18 is inflated to effect a seal between balloon 18 and the interior wall 12 of lumen 10.

Once the target site is isolated from the rest of the vasculature, the supply of electrically conductive fluid 30 is continuously delivered to region 8 and balanced with the aspiration of fluid from the site of intended recanalization. The active electrode(s) 32 is (are) then energized by applying a high frequency voltage between active electrode(s) 32 and return electrode or guide wire 28. A high electric field is created at the surface of active electrode(s) 32 which causes the volumetric removal or ablation or target tissue in close proximity with active electrode(s) 32. The flow of electrical current between return electrode 28 and active electrode(s) 32 is shown by current flux lines 62 in FIG. 2B. As the occlusive media 14 is ablated, gaseous products are generated (not shown) which are entrained in the electrically conducting fluid 30 and removed through aspiration lumen 58 (not shown). The current flux lines 62 are generally confined to the central portion of tissue ablation region 8 because they generally flow inward towards return electrode 28 and because the occlusive media 14 generally shields the outer region of lumen (including stent 16) from flux lines 62. This minimizes undesirable interaction between the electrical current and stent 16.

Referring to FIG. 2C, this ablation procedure is continued until the desired length of the lumen containing occlusive media is recanalized. During the recanalization process, the products of ablation are confined between proximal balloon 40 and distal balloon 18 to minimize, for example, the injection of any non-condensible gaseous products of ablation into the blood stream which could otherwise lead to the formation of injurious or life-threatening emboli. Once the occlusive media 14 has been volumetrically removed (i.e., ablated), the energy application is suspended, the valve on the aspiration lumen is closed, control valve 104 is closed and balloons 18, 40 are deflated. The time period from the initial inflation of balloons 18, 40 to the deflation of these balloons is typically about 15–45 seconds, depending on the length and the extent of occlusion in the vessel. For longer occlusions, the above process may be repeated several times with intervals of no balloon inflation so that vital oxygen-bearing blood can be reperfused through the zone of intended recanalization to preserve the tissue distal to the recanalization zone.

Figure 3A:
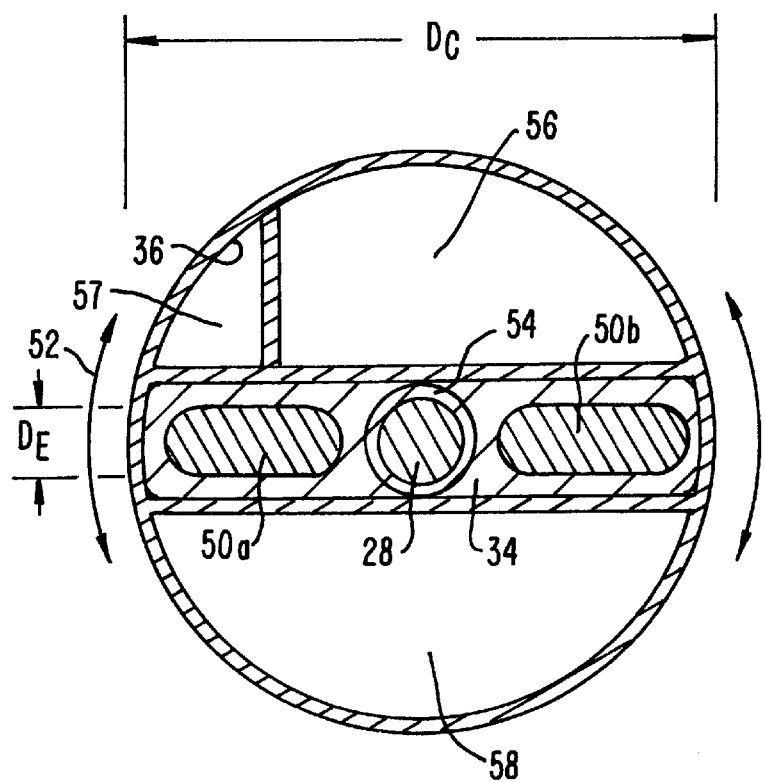
FIGS. 3A and 3B are transverse and longitudinal cross-sectional views, respectively, of a first embodiment of the distal portion of the catheter.
Figure 3B:
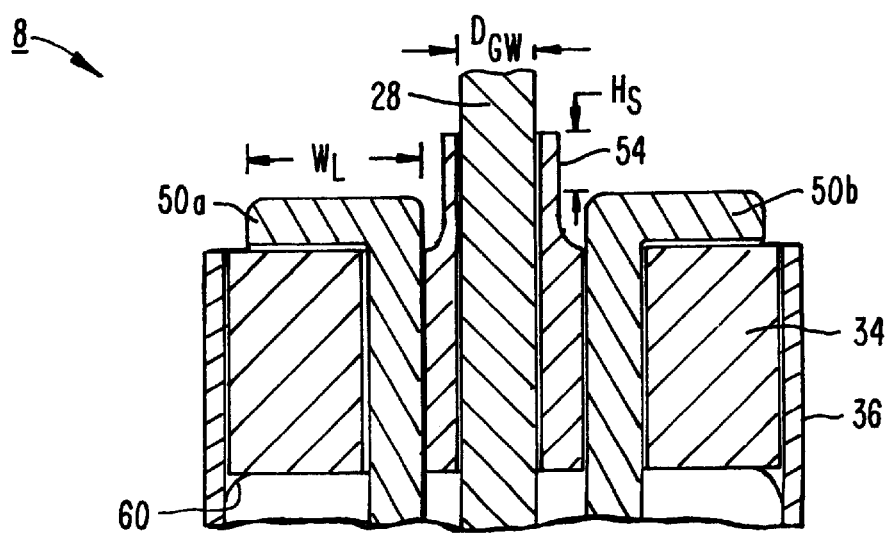

A first embodiment of tissue ablation region 8 of catheter 6 is shown in FIGS. 3A and 3B. As shown, two active electrodes 50a and 50b are secured within an electrically insulating support member 34. The electrodes 50a, 50b are preferably composed of a refractory, electrically conductive metal or alloy, such as platinum, titanium, tantalum, tungsten, stainless steel and the like. The support member 34 is secured to the distal end of catheter 6 with a biocompatible adhesive 60 between support member 34 and outer sleeve 36. An inorganic electrically insulating sleeve 54 preferably extends above the distal plane of active electrodes 50a, 50b by a distance $H_s$. A central lumen in support member 34 provides a passageway for guide wire 28 that permits axial displacement and rotation of tissue ablating region 8 relative to guide wire 28.

In an exemplary embodiment, the support member 34 will comprise an inorganic insulator, such as ceramic, glass, glass/ceramic or a high resistivity material, such as silicon or the like. An inorganic material is generally preferred for the construction of the support member 34 since organic or silicone based polymers are known to rapidly erode during sustained periods of the application of high voltages between electrodes 50 and the return electrode 28 during tissue ablation. However, for situations in which the total cumulative time of applied power is less than about one minute, organic or silicone based polymers may be used without significant erosion and loss of material of the support member 34 and, therefore, without significant reduction in ablation performance.

As shown in FIG. 3A, an irrigation lumen 56 and an aspiration lumen 58 are provided to inject electrically conducting fluid 30 and remove gaseous products of ablation 48 from the site of recanalization. An additional fluid lumen 57 provides fluid communication between inflation syringe 108 and proximal balloon 40. This fluid lumen 57 is filled with a sealant in those portions of the catheter distal to proximal balloon 40.

In use with the present invention, catheter 6 is rotated about 180 degrees clockwise and then about 180 degrees counter clockwise as the electrodes 50 are energized by generator 80 (FIG. 1) to effect ablation of the occlusive media. Using a reciprocating rotational motion combined with a small pressure to advance tissue ablation region 8 through the longitudinal length of the occlusive media 14 allow recanalization of the occluded vessel as described with reference to FIGS. 2A–2C. The cross-sectional shape of the active electrodes may be round wires as shown in FIG. 3B, or they may have shaped surfaces to enhance the electric field intensity at the distal surfaces of the active electrodes 50. Suitable electrode designs for use with the present invention may be found in co-pending, commonly assigned application Ser. No. 08/687,792, filed Jul. 19, 1996 (Attorney Docket No. 16238-001600), the complete disclosure of which is incorporated herein by reference for all purposes.

Return electrode 28 comprises an electrically conducting material, usually metal, which is selected from the group consisting of stainless steel alloys, platinum or its alloys, titanium or its alloys, molybdenum or its alloys, and nickel or its alloys. The return electrode 28 may be composed of the same metal or alloy which forms the active electrodes 50 to minimize any potential for corrosion or the generation of electrochemical potentials due to the presence of dissimilar metals contained within an electrically conductive fluid 30, such as isotonic saline (discussed in greater detail below).

Figure 4A:
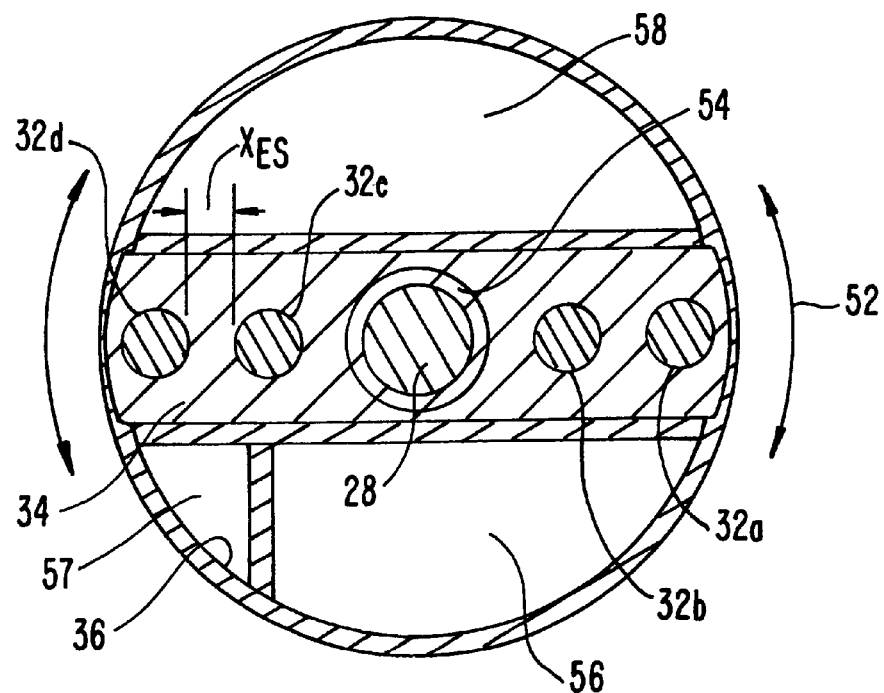
FIGS. 4A and 4B are transverse and longitudinal cross-sectional views, respectively, of a second embodiment of the distal portion of the catheter.
Figure 4B:
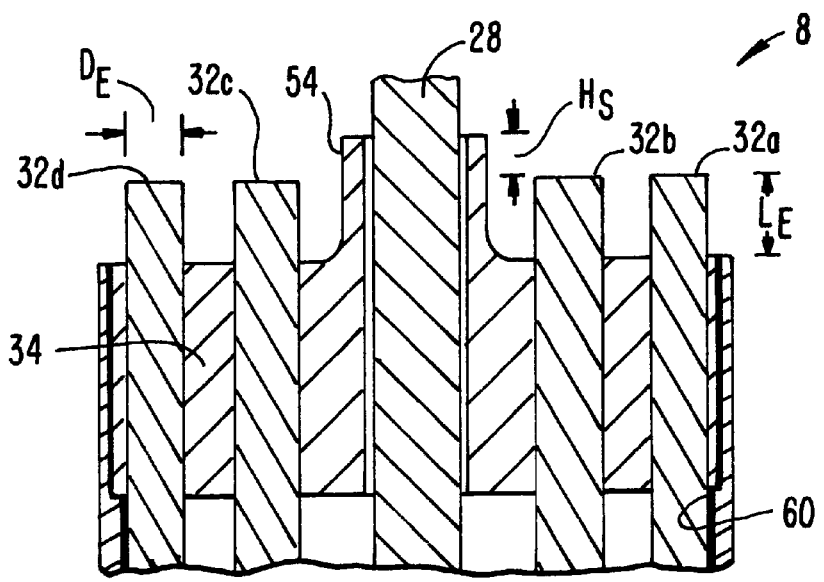

Referring now to FIGS. 4A and 4B, a second embodiment of tissue ablation region 8 of catheter 6 will now be described. In this embodiment, four active electrodes 32a, 32b, 32c, 32d are secured within an inorganic electrically insulating support member 34. Similar to the previous embodiment, support member 34 is secured to the distal end of catheter 6 with a biocompatible adhesive 60 between support member 34 and outer sleeve 36. An inorganic electrically insulating sleeve 54 preferably extends above the distal plane of active electrodes 50a, 50b by a distance Hs. A central lumen in support member 34 provides a passageway for guide wire 28 that permits axial displacement and rotation of tissue ablating region 8 relative to guide wire 28. As shown in FIG. 4A, an irrigation lumen 56 and an aspiration lumen 58 are provided to inject electrically conducting fluid 30 and remove gaseous products of ablation 48 from the site of recanalization. An additional fluid lumen 57 provides fluid communication between inflation syringe 108 and proximal balloon 40. This fluid lumen 57 is filled with a sealant in those portions of the catheter distal to proximal balloon 40.

In use, catheter 6 is rotated about 180 degrees clockwise and then about 180 degrees counter clockwise as the electrodes 32 are energized by generator 80 (FIG. 1) to effect ablation of the occlusive media. Using a reciprocating rotational motion combined with a small pressure to advance tissue ablation region 8 through the longitudinal length of the occlusive media 14 allow recanalization of the occluded vessel as described with reference to FIGS. 2A–2C. The cross-sectional shape of the active electrodes may be round wires as shown in FIG. 4B, or they may have shaped surfaces to enhance the electric field intensity at the distal surfaces of the active electrodes 32 as described co-pending, commonly assigned application Ser. No. 08/687,792, filed Jul. 19, 1996 (Attorney Docket No. 16238-001600), the complete disclosure of which has previously been incorporated herein by reference.

Figure 5A:
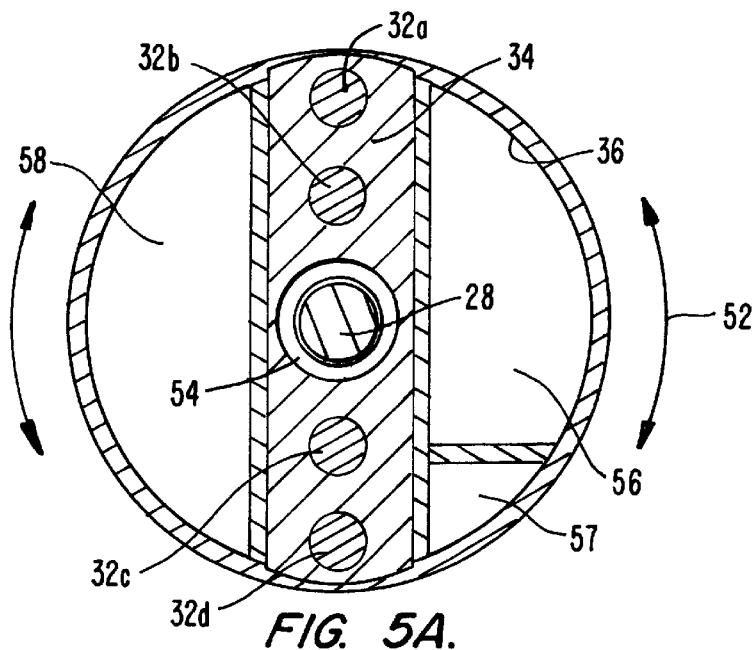
FIGS. 5A and 5B are transverse and longitudinal cross-sectional views, respectively, of the second embodiment of the distal portion of the catheter further illustrating the inflow of conductive liquid and aspiration of conductive liquid and gaseous products.
Figure 5B:
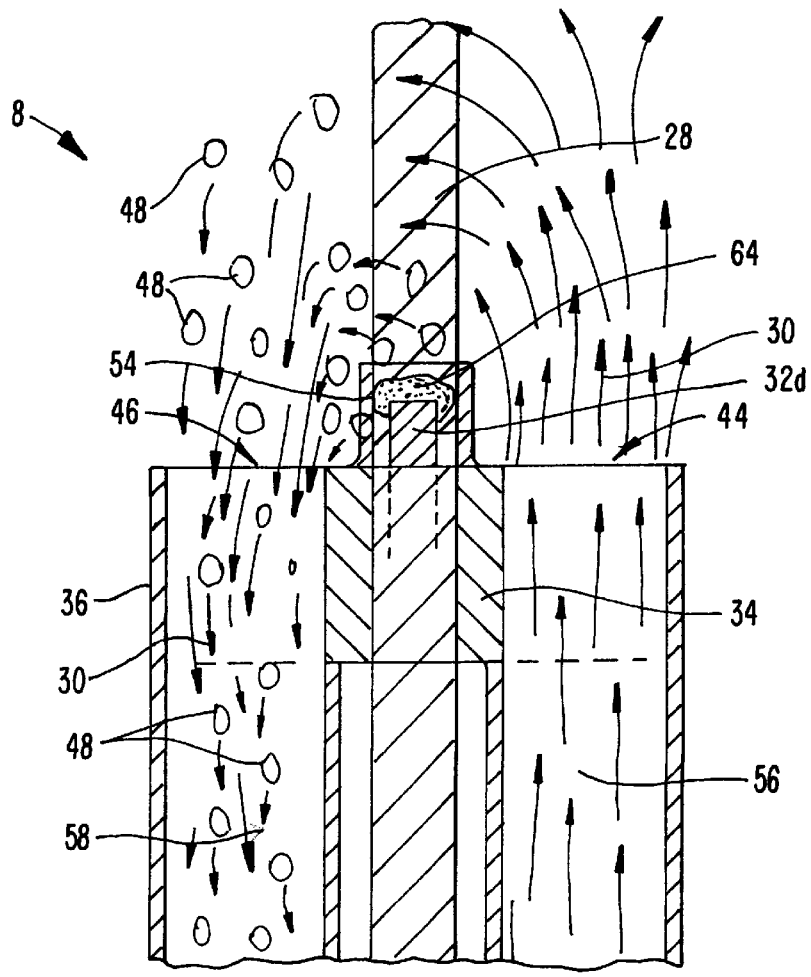

The second embodiment of FIGS. 4A and 4B is illustrated in greater detail in FIGS. 5A and 5B. As shown, electrically conductive fluid flows through irrigation lumen 56 of catheter 6 to and through irrigation port 44 and subsequently surrounds the target tissue site (i.e., occlusive media 14). When high frequency voltage is applied between the return electrode 28 and active electrodes 32, a vapor layer 64 forms at and around active electrodes 32 with concomitant volumetric removal (ablation) of the occlusive media 14. A more detailed description of this phenomena can be found in commonly assigned, co-pending application Ser. No. 08/561,958, filed on Nov. 22, 1995 (Attorney Docket 16238-000700), the complete disclosure of which has previously been incorporated herein by reference. The occlusive media 14 is decomposes into gaseous products of ablation 48 which are entrained in electrically conducting fluid 30 and evacuated through aspiration port 46 and to the proximal end of catheter 6 via aspiration lumen 58.

Figure 6A:
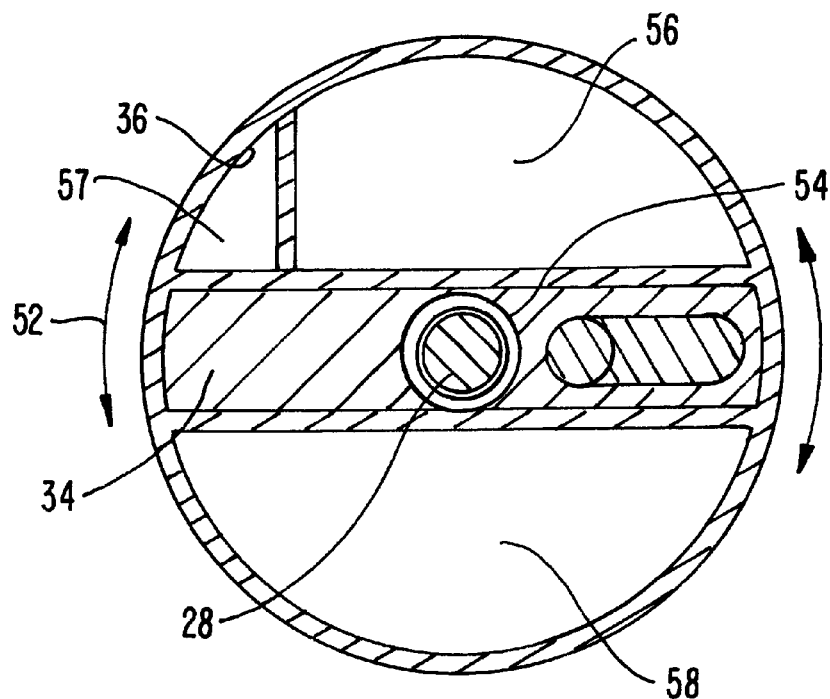
FIGS. 6A and 6B are transverse and longitudinal cross-sectional views, respectively, of a third embodiment of the distal portion of the catheter.
Figure 6B:
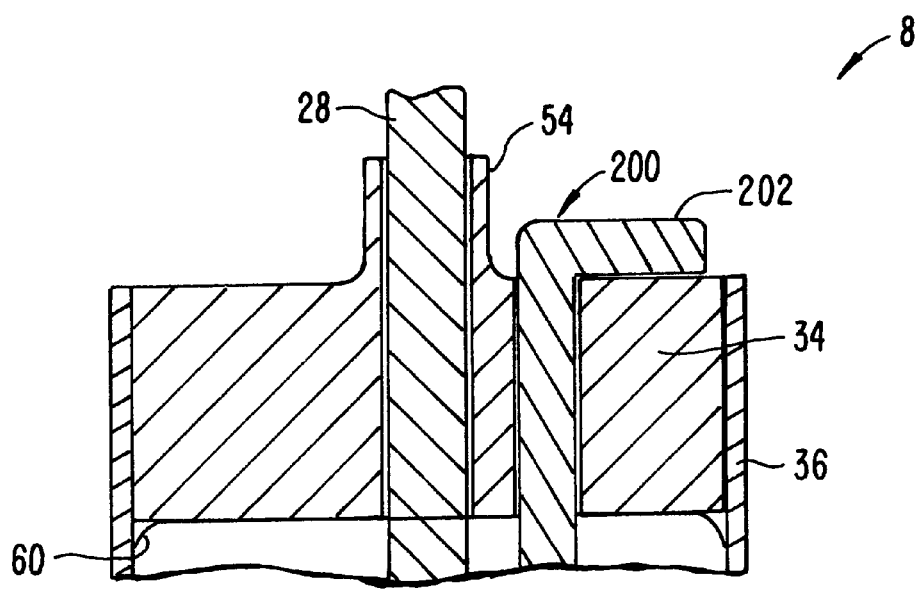

A third embodiment of tissue ablation region 8 is illustrated in FIGS. 6A and 6B. Many of the elements of this embodiment are the same as previous embodiments, and therefore will not be repeated. As shown, a single active electrode 200 is secured within support member 34. Active electrode 200 preferably has an L-shaped distal end so that a distal portion 202 of electrode 200 extends radially outward along the distal surface of support member 34. As before, electrode 200 is rotated in both directions, as the region 8 is advanced through the lumen to recanalize the lumen.

Figure 7A:
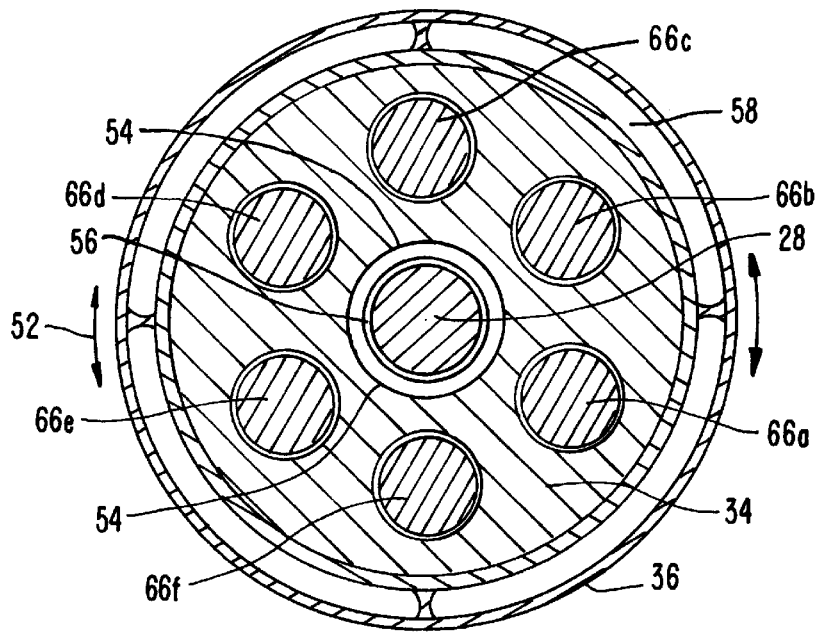
FIGS. 7A and 7B are transverse and longitudinal cross-sectional views, respectively, of a fourth embodiment of the distal portion of the catheter.
Figure 7B:
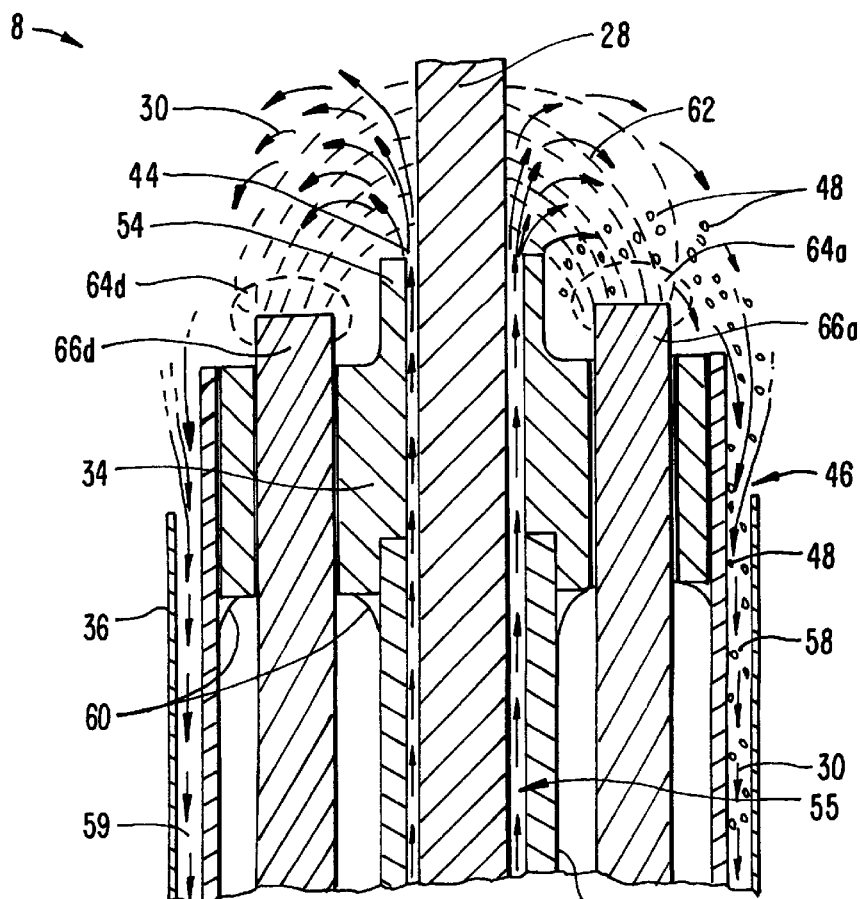

A fourth embodiment of tissue ablation region 8 is illustrated in FIGS. 7A and 7B. Many of the elements of this embodiment are the same as previous embodiments, and therefore will not be repeated. As shown, six active electrodes 66a–66f are secured within inorganic support member 34. An annular irrigation lumen 55 and an aspiration lumen 59 are provided to inject electrically conducting fluid 30 and remove gaseous products of ablation 48 from the site of recanalization. When high frequency voltage is applied between the return electrode 28 and active electrodes 66, a vapor layer 64 forms at and around active electrodes 66 with concomitant volumetric removal (ablation) of the occlusive media 14. For this embodiment and that shown in FIGS. 8A and 8B, rotation may be limited to +− 30 degrees due to the greater number and circumferential distribution of active electrodes. The power or current supplied to each electrode may be individually controlled by active or passive mechanisms as previously described in commonly assigned, co-pending application Ser. No. 08/561,958, filed on Nov. 22, 1995 (Attorney Docket 16238-000700). The occlusive media 14 is decomposed into gaseous products of ablation 48 which are entrained in electrically conducting fluid 30 and evacuated through aspiration port 46 and onto the proximal end of catheter 6 via aspiration lumen 59. As shown in FIG. 7b, the current flux lines 62 are confined to the central portions of tissue ablation region 8.

Figure 8A:
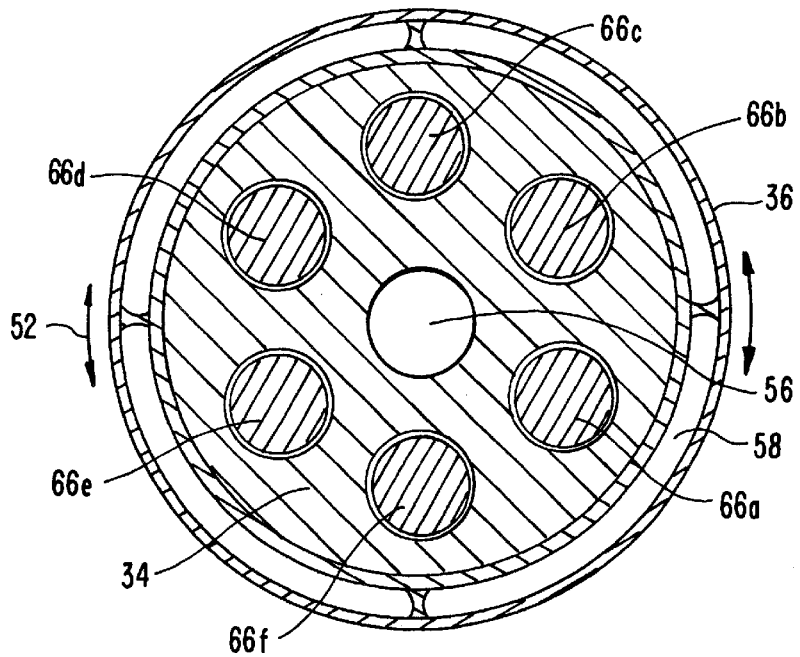
FIGS. 8A and 8B are transverse and longitudinal cross-sectional views, respectively, of a fifth embodiment of the distal portion of the catheter.
Figure 8B:
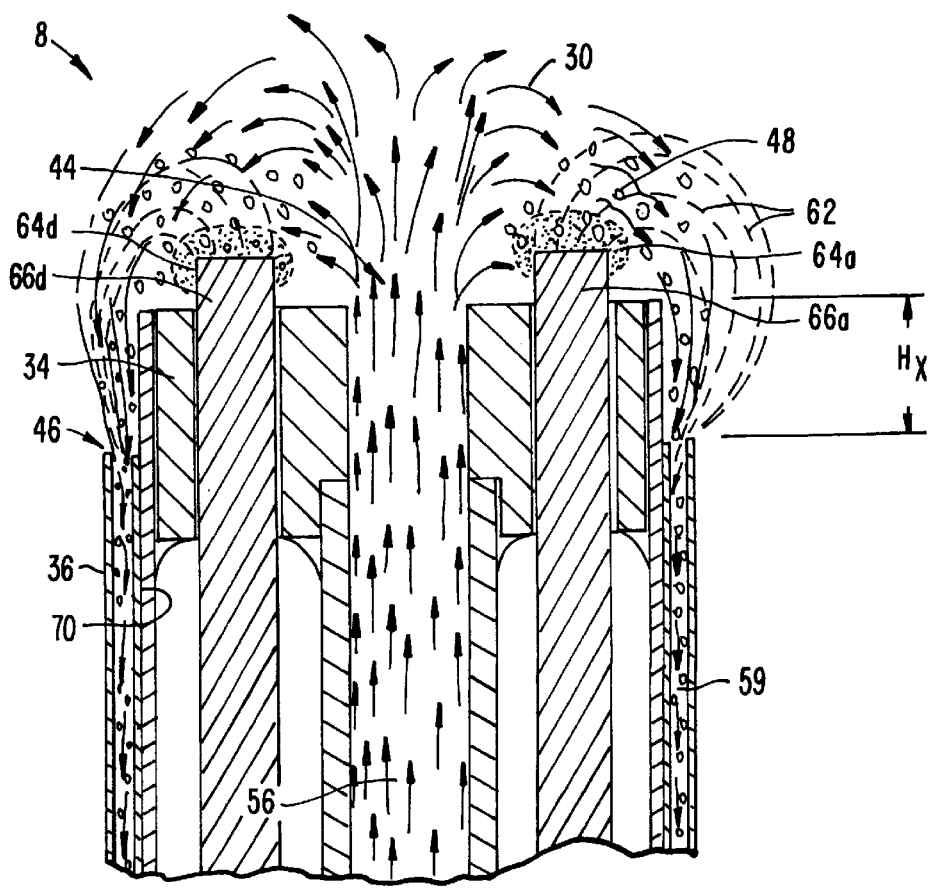

FIGS. 8A and 8B illustrate a fifth embodiment of the present invention. This embodiment is similar to the fourth embodiment in that six active electrodes 66a–66f are secured within inorganic support member 34. A return electrode 70 (e.g., metal sleeve) is positioned proximal to the active electrodes 66a–66f by a distance $H_x$. In this embodiment, current flux lines 62 travel proximally from the distal tips of electrodes 66 to the proximally spaced return electrode 70.

Figure 9A:
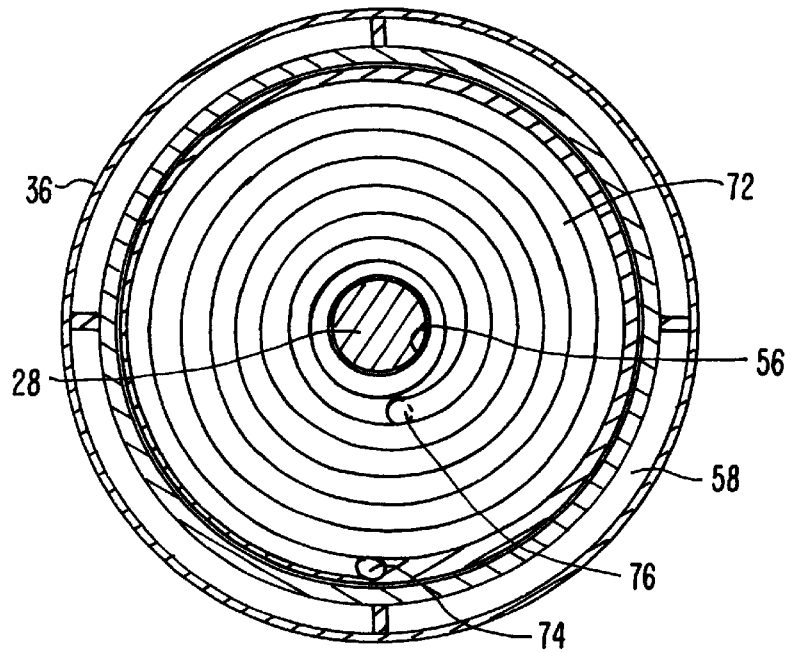
FIGS. 9A and 9B are transverse and longitudinal cross-sectional views, respectively, of a sixth embodiment of the distal portion of the catheter.
Figure 9B:
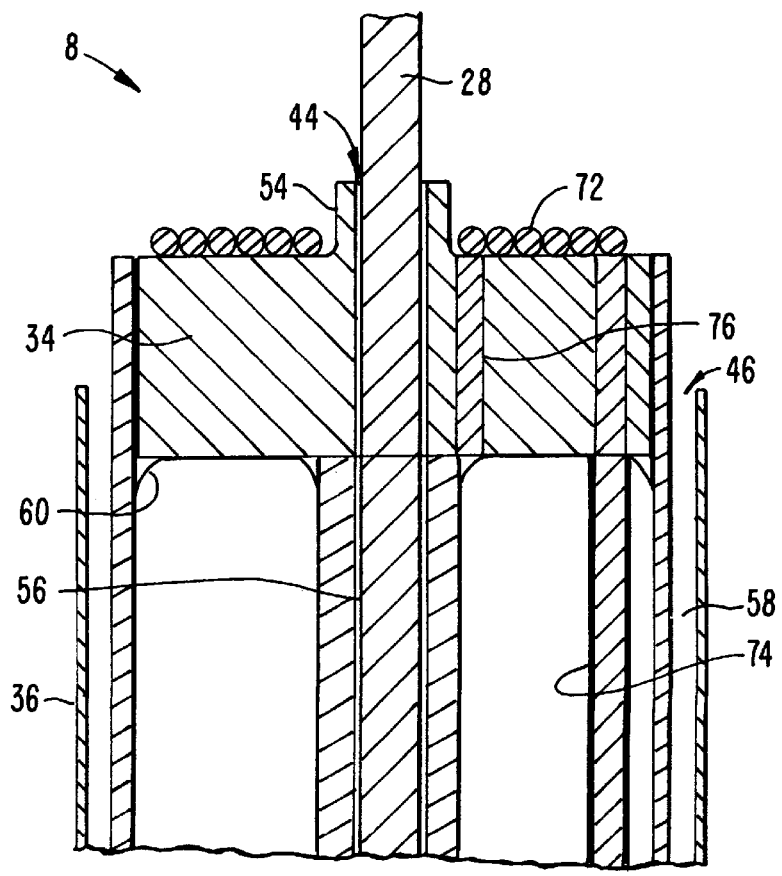

Referring to FIGS. 9A and 9B, a sixth embodiment of the invention will now be described. As shown, a single active electrode 72 is secured within inorganic support member 34. In this embodiment, active electrode 72 comprises a coiled wire having a plurality of concentric coils tightly and helically wrapped and secured on support member 34 (FIG. 9B). Preferably, the helical coil extends around return electrode 28 in concentric configuration, as shown in FIG. 9A.

Figure 10A:
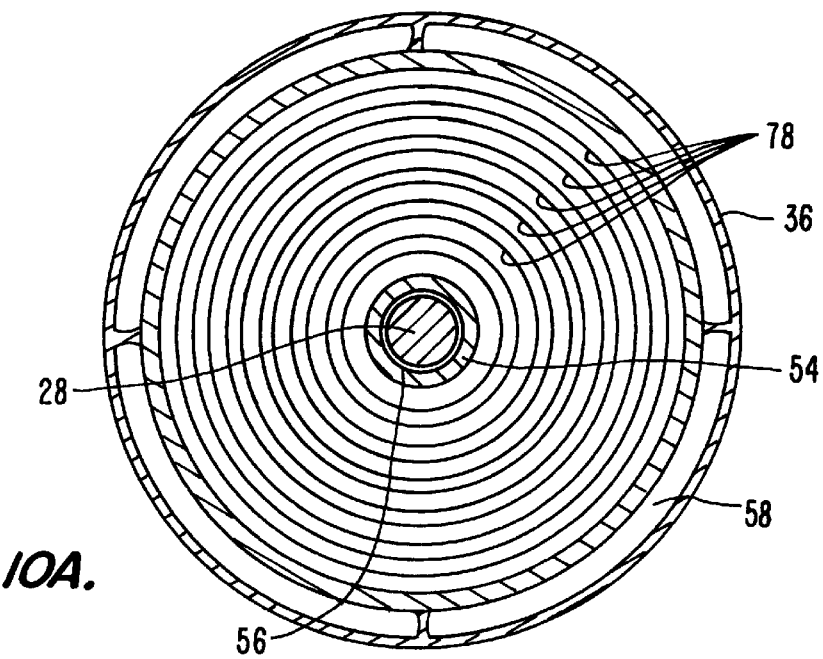
FIGS. 10A and 10B are transverse and longitudinal cross-sectional views, respectively, of a seventh embodiment of the distal portion of the catheter.
Figure 10B:
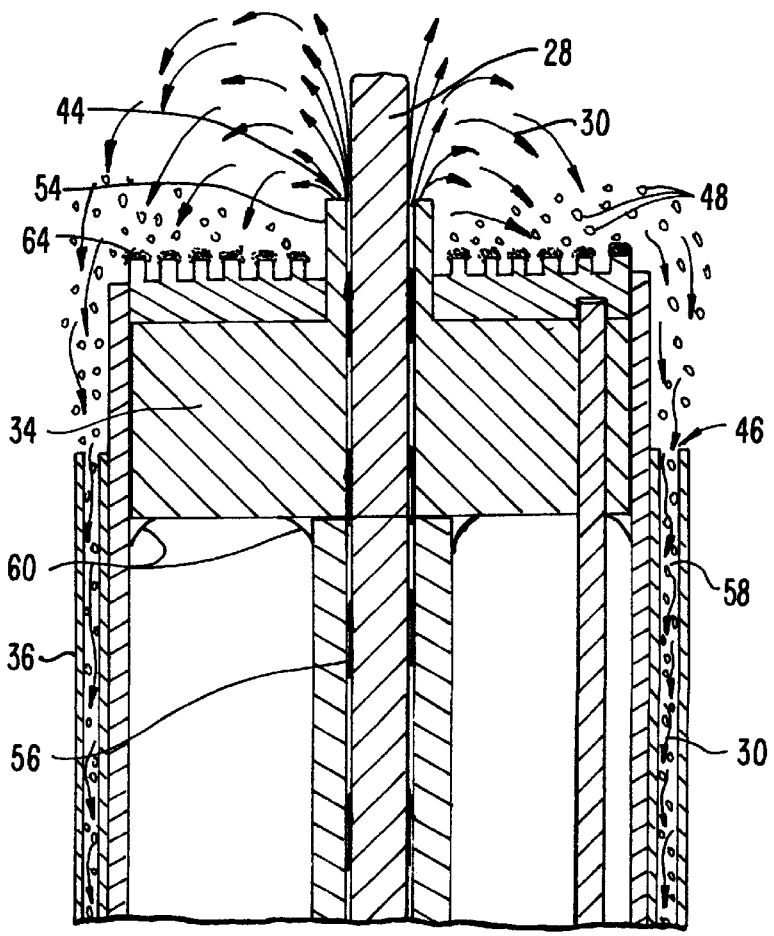

A seventh embodiment of the invention is shown in FIGS. 10A and 10B. This embodiment is similar to the sixth embodiment except that the single active electrode 73 defines a series of concentric machined grooves 75 to form concentric circular electrodes 78 surrounding return electrode 28. The distal edges of electrodes 78 generate regions of high electric field intensities when high frequency voltage is applied between return electrode 28 and concentric active electrodes 78. A vapor layer 64 forms at and around active electrodes 78 with concomitant volumetric removal (ablation) of the occlusive media. The embodiments of FIGS. 9 and 10 are usually advanced through the occlusive media without rotation.

What is claimed is:

1. A method for maintaining patency in a body passage having an intraluminal prosthesis with a cylindrical wall positioned therein, wherein occlusive media has grown through or around the cylindrical wall of the prosthesis into the body passage, the method comprising:

positioning an active electrode near or at the occlusive media;

delivering electrically conductive fluid to the prosthesis such that the active electrode is substantially surrounded by the electrically conductive fluid; and applying high frequency voltage to the active electrode to selectively remove the occlusive media without directly applying current to the prosthesis.

2. The method of claim 1 further comprising applying high frequency voltage to the active electrode and a return electrode positioned within the body lumen and spaced from the occlusive media such that an electrical current flows from the active electrode, through the the electrically conductive fluid, and to the return electrode.

3. The method of claim 2 wherein the return electrode is positioned radially inward from the active electrode such that the electrical current flows from the active electrode radially inward to the return electrode, thereby inhibiting current flow through the prosthesis.

4. The method of claim 2 further comprising generating a current flow path through the electrically conducting fluid between the return electrode and the active electrode.

5. The method of claim 1 further comprising advancing a catheter body into the lumen to position the active electrode in close proximity with the occlusive media.

6. The method of claim 5 wherein the active electrode is positioned at a distal portion of the catheter body, the method further comprising:

reciprocally rotating at least the distal portion of the catheter body during the applying step; and advancing the catheter body through the vacancy left by the ablated occlusive media.

7. The method of claim 1 further comprising applying high frequency voltage to an electrode array of electrically isolated active electrodes and a return electrode such that an electrical current flows from each of the active electrodes, through the electrically conductive fluid, and to the return electrode through the current flow path.

8. The method of claim 7 further comprising independently controlling current flow from at least two of the active electrodes based on impedance between the active electrodes and the return electrode.

9. The method of claim 1 further comprising:

before the applying step, fluidly isolating a region around the occlusive media within the body passage to confine products of ablation within said region; and aspirating said ablation products from the body passage.

10. The method of claim 9 wherein the fluidly isolating step comprises:

advancing a first balloon to a portion of the body passage proximal to said region;

inflating said first balloon to inhibit fluid flow therethrough;

positioning a second balloon at a portion of the body passage distal to said region; and inflating said second balloon to inhibit fluid flow therethrough.

11. The method of claim 1 further comprising:

before the applying step, delivering electrically conductive fluid to a region around the occlusive media to displace naturally occurring bodily fluid from said region; and fluidly isolating said region to confine the electrically conducting fluid within said region.

12. The method of claim 11 further comprising:

during the applying step, supplying electrically conductive fluid to said region; and entraining gaseous products of ablation within the electrically conductive fluid and aspirating the gaseous ablation products from said region.

13. The method of claim 1 farther comprising advancing a catheter body into the lumen to position the active electrode in close proximity with the tissue ingrowth.

14. The method of claim 1 further comprising confining the electrical current flow to a central portion of the body passage.

15. A method for recanalizing a body lumen having an intraluminal prosthesis disposed therein, the body lumen having tissue ingrowth in or around the prosthesis, the method comprising:

positioning an active electrode into at least close proximity with the tissue ingrowth in the presence of an electrically conducting fluid;

positioning a return electrode within the electrically conducting fluid to generate a current flow path between the tissue ingrowth and the return electrode; and applying high frequency voltage to the active electrode and the return electrode such that an electrical current flows from the active electrode, through the region of the tissue ingrowth, and to the return electrode through the current flow path.

16. The method of claim 13 further comprising applying sufficient high frequency voltage to the active electrode and the return electrode to generate high electric field intensities around the active electrode, wherein the electric field intensities are sufficient to cause molecular disintegration of tissue structure.

17. The method of claim 13 wherein the high frequency voltage is sufficient to vaporize the fluid in a thin layer over at least a portion of the active electrode and induce the discharge of energy from the vapor layer.

18. The method of claim 17 wherein at least a portion of the energy induced from the vapor layer is in the form of photons having a wavelength in the ultraviolet spectrum or energetic electrons.

19. The method of claim 13 further comprising applying high frequency voltage to an electrode array of electrically isolated active electrodes and a return electrode such that an electrical current flows from each of the active electrodes, through the region of the tissue ingrowth, and to the return electrode through the current flow path.

20. The method of claim 19 wherein the electrode array comprises between 4 to 50 active electrodes.

21. The method of claim 13 wherein the high frequency voltage is at least 300 volts peak to peak.

22. The method of claim 13 wherein the high frequency voltage is in the range from 600 to 1400 volts peak to peak.

23. The method of claim 13 further comprising directing an electrically conducting fluid along a fluid path past the return electrode and to the active electrode to generate the current flow path between the active electrode and the return electrode.

24. The method of claim 13 further comprising submerging the active electrode and the return electrode within naturally occurring electrically conducting fluid within the body lumen.

25. The method of claim 13 wherein the electrically conducting fluid comprises isotonic saline.

\* \* \* \* \*